United States Patent [19]
Gunnarsson et al.

[11] Patent Number: 5,310,913
[45] Date of Patent: May 10, 1994

[54] DERIVATIVES OF QUINOLINE-3-CARBOXANILIDE

[75] Inventors: Per O. Gunnarsson; Torbjörn Stalhandske, both of Helsingborg; Kerstin Strandgarden, Vallakra; Karl-Erik Lundvall, Angelholm; Kaj Johansson, Helsingborg, all of Sweden

[73] Assignee: Kabi Pharmacia Aktiebolag, Sweden

[21] Appl. No.: 102,393

[22] Filed: Aug. 5, 1993

Related U.S. Application Data

[63] Continuation of Ser. No. 941,866, Sep. 8, 1992, which is a continuation of Ser. No. 651,234, Mar. 22, 1991.

[30] Foreign Application Priority Data

Jun. 9, 1989 [SE] Sweden ................ 8902076

[51] Int. Cl.$^5$ .......................................... C07D 215/56
[52] U.S. Cl. .................................................. 546/155
[58] Field of Search ....................... 514/312; 546/155

[56] References Cited

U.S. PATENT DOCUMENTS

| | | | |
|---|---|---|---|
| 3,960,868 | 1/1976 | Ferrini et al. | 546/155 |
| 4,547,511 | 10/1985 | Eriksoo et al. | 514/312 |
| 4,659,603 | 5/1985 | Grohe | 424/88 |
| 4,738,971 | 4/1988 | Eriksoo et al. | 546/155 |
| 5,084,462 | 1/1992 | Ackerman et al. | 514/312 |
| 5,175,151 | 12/1992 | Afonso et al. | 546/155 |

FOREIGN PATENT DOCUMENTS

| | | | |
|---|---|---|---|
| 0152966 | 6/1990 | Japan | 546/155 |
| 90-15052 | 12/1990 | PCT Int'l Appl. | |

OTHER PUBLICATIONS

Ilbaeck, et al. Chem. Abstr. vol. 110, entry 88192n (1988).
Jonsson et al. Chem. Abstr. vol. 110 entry 476z (1988).
Morahan et al. Chem. Abstr. vol. 109 entry 122145r (1987).
Larsson et al. Chem. Abstr. vol. 107 entry 109005j (1987).
Tarkowski et al. Chem. Abstr. vol. 106 entry 43654r (1986).
Kalland, Chem. Abstr. vol. 105 entry 35258d (1986).
Staalhandske et al. Chem. Abstr. vol. 105 entry 313r (1986).
Kelland et al. Chem. Abstr. vol. 103 entry 115873z (1986).
Yoshizari et al, Chem. Abstr. vol. 113, abstracting JP 0,2 152966 (Jun. 1990).
Harning, Chem. Abstr. vol. 112 entry 191574d (1989).
Kleinau et al. Chem. Abstr. vol. 112 entry 356b (1989).
Carlsten, Chem. Abstr. vol. 111 entry 224959t (1989).
Spetz-Hagberg et al. Chem. Abstr. vol. 111 entry 146465h (1989).

(List continued on next page.)

*Primary Examiner*—Donald G. Daus
*Attorney, Agent, or Firm*—Pravel, Hewitt, Kimball & Krieger

[57] ABSTRACT

Compounds having formula

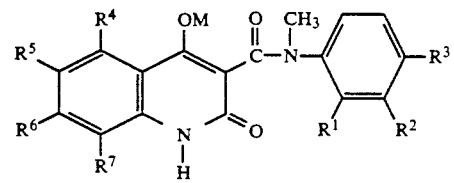

wherein $R^1$, $R^2$, $R^3$, $R^4$, $R^5$, $R^6$ and $R^7$ are selected from the group consisting of hydrogen, hydroxy and methoxy. At most one of $R^1$, $R^2$ and $R^3$ and at most one of $R^4$, $R^5$, $R^6$ and $R^7$ is selected from the group consisting of hydroxy and methoxy. M is selected from the group consisting of hydrogen and pharmaceutically acceptable inorganic or organic cations or tautomeric forms thereof. The compounds have immunomodulating activity.

8 Claims, No Drawings

OTHER PUBLICATIONS

Bjoerk et al. Chem. Abstr. vol. 111 entry 33310q (1989).
Gerdin et al. Chem. Abstr. vol. 111 entry 17327v (1989).
Iibaek et al. Chem. Abstr. vol. 110 entry 205297p (1989).
Wanders et al. Chem. Abstr. vol. 110 entry 185373e (1989).
Dorlands Medical Dictionary, 26 Ed., Philadelphia, Saunders, 1981, p. 654.
Jones (ed), Quinolines, Part 1 Interscience pp. 93–95 (1977).
Bicker et al., "Comparative Investigations of Various Immunoregulatory Substances in the Delayed Type Hypersensitivity Test of the Mouse", 6 *J. Immunopharmacology* 57 (1984).
Tarkowski, et al. "Successful Treatment of Autoimmunity in MRL/1 Mice with LS-2616, A New Immunomodulator," 29 *Arthritis and Rheumatism* 1405 (1956).
Part 1 The Basis of Medicinal Chemistry, Burger's Medicinal Chemistry, 4th Ed. Interscience pp. 146–153 (1980).

DERIVATIVES OF QUINOLINE-3-CARBOXANILIDE

This is a continuation of co-pending application Ser. No. 07/941,866 filed on Sep. 8, 1992 which is a continuation of co-pending application Ser. No. 07/651,234 filed on Mar. 22, 1991.

The present invention relates to novel quinoline-3-carboxanilide derivatives, processes for their preparation, pharmaceutical compositions containing them and methods of treatment therewith.

The object of this invention is to provide novel compounds which can be used in therapy of diseases which respond to treatment with immunomodulating agents.

PRIOR ART

A group of heterocyclic carboxamides which increase the activity of the immune system is disclosed in U.S. Pat. No. 4,547,511. A compound which is included in said patent is roquinimex, also known by the code no LS 2616.

The immunomodulating activity of LS 2616 is described further in Tarkowski, et al., 29 *Arthritis Rheum.* 1405 (1986).

DISCLOSURE OF THE INVENTION

It has been found that compounds of the general formula I possess useful intnunomodulating activity. These compounds, unlike those described in the above mentioned U.S. patent, have no substituents on the nitrogen atom of the quinoline ring.

It is known that N-methyl groups are converted by metabolyic reactions to formaldehyde which is a toxic substance. The compounds of the general formula I thus have a lower potential to produce toxic metabolites, which is an advantage especially in individuals with impaired liver function.

The compounds of the general formula I also show higher chemical stability in free form compared with corresponding known compounds cited above. This makes them more useful in certain types of pharmaceutical compositions, e g those intended for transdermal application where it is essential that the active ingredient be in neutral form.

SUMMARY OF THE INVENTION

The invention comprises compounds having the general formula

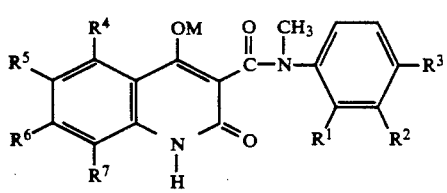

wherein $R^1$, $R^2$, $R^3$, $R^4$, $R^5$, $R^6$ and $R^7$ are selected from the group consisting of hydrogen, hydroxy and methoxy. At most one of $R^1$, $R^2$ and $R^3$ and at most one of $R^4$, $R^5$, $R^6$ and $R^7$ is selected from the group consisting of hydroxy and methoxy.

M is selected from the group consisting of hydrogen and pharmaceutically acceptable inorganic or organic cations.

As it is apparent to one skilled in the art the compounds of the general formula I may exist in different tautomeric forms.

METHODS OF PREPARATION

The compounds of the general formula I are prepared by conventional methods.

METHOD I

Compounds of the general formula I are prepared by reacting a carboxylic acid II or a reactive derivative thereof

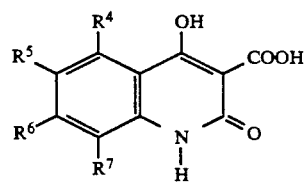

with an amine of the general formula III or a reactive derivative thereof

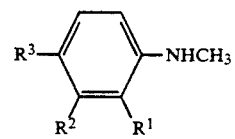

Having a reactive derivative of II the reaction may be carried out by mixing the reagents in an inert solvent medium at a temperature between 0° and 200° C. depending on the reactivity of the reactive derivative of the carboxylic acid used. As such reactive derivatives the following conventional types may be mentioned: acid chlorides, anhydrides, mixed anhydrides with aliphatic and aromatic sulphonic acids, and reactive derivatives obtained with carbodiimides and similar reagents.

The carboxylic acids II and the reactive derivatives thereof may be prepared by conventional methods as described in *Quinolines Part* 1, p. 93–318, G. Jones (Ed.) John Wiley & Sons (1977). The amines III are known compounds.

METHOD II

A compound of the general formula I wherein at least one of the groups $R^1$—$R^7$ is a hydroxy group and none of $R^1$—$R^7$ is a methoxy group may be prepared by deal kylation of a compound of the general formula having lower alkoxy (preferably methoxy) groups in positions where hydroxy groups are desired.

The dealkylation is preferably carried out with boron tribromide.

The starting materials of the general formula I having methoxy groups in desired positions may be prepared using the type of reaction described in Method I above and in references given there.

EXAMPLE 1

N,N-dicyklohexylcarbodiimide (2.2 parts) is added to a mixture consisting of 1,2-dihydro-4-hydroxy-2-oxo-quinoline-3-carboxylic acid (2.0 parts), N-metylaniline (1.1 parts) and dry toluene (25 parts) while stirring. The stirring is continued at 110° C. for 4 hrs. The reaction mixture is cooled to room temperature and the precipitate formed is filtered off. The precipitate is dissolved at pH 8.2 in 2M sodium hydroxide solution and clarified by filtration to remove the N,N-dicyklohexylurea formed. The solution is acidified with hydrochloric acid solution and the precipitate formed is filtered off. The precipitate is washed with water and methanol and dried to give N-methyl-N-phenyl-1,2-dihydro-4-hydroxy-2-oxo-quinoline-3-carboxamide, m p>300° C. (1:1).

In essentially the same manner the following compounds are obtained:

N-methyl-N-(4-methoxyphenyl)-1,2-dihydro-4-hydroxy-2-oxo-quinoline-3-carboxamide, m p>250° C. (1:2)

N-methyl-4-phenyl-1,2-dihydro-4-hydroxy-6-methoxy-2-oxo-quinoline-3-carboxamide, m p>250° C. (1:3)

N-methyl-N-(4-methoxyphenyl)-1,2-dihydro-4-hydroxy-6-methoxy-2-oxo-quinoline-3-carboxamide, m p>250° C. (1:4)

N-methyl-N-(3-methoxyphenyl)-1,2-dihydro-4-hydroxy-7-methoxy-2-oxoquinoline-3-carboxamide, m p>250° C. (1:5).

EXAMPLE 2

N-methyl-N-(4-methoxyphenyl)-1,2-dihydro-4-hydroxy-2-oxo-quinoline-3-carboxamide (6.5 parts) is suspended in 100 parts of methylene chloride and the mixture obtained is cooled to −60° C.

A solution of boron tribromide (20 parts) in methylene chloride (100 parts) is added dropwise while stirring. The mixture is allowed slowly to assume room temperature and is then poured into ice-water. The precipitate obtained is filtered off, washed with water and dried to give N-methyl-N-(4-hydroxyphenyl)-1,2-dihydro-4-hydroxy-2-oxo-quinoline-3-carboxamide, m p 250° C. (2:1).

In essentially the same manner the following compounds are obtained:

N-methyl-N-phenyl-1,2-dihydro-4,6-dihydroxy-2-oxo-quinoline-3-carboxamide (2:2)

N-methyl-N-phenyl-1,2-dihydro-4,7-dihydroxy-2-oxo-quinoline-3-carboxamide (2:3)

N-methyl-N-(4-hydroxy-phenyl)-1,2-dihydro-4-hydroxy-2-oxo-quinoline-3-carboxamide (2:4)

N-methyl-N-(4-hydroxy-phenyl)-1,2-dihydro-4,6-dihydroxy-2-oxo-quinoline-3-carboxamide (2:5)

EXAMPLE 3

This example illustrates the effect of the compounds of the general formula I in the oxazolone induced hypersensitivity test in mice. A modification of a method described in Bicker et al., 6 *J. Immunopharmacology*, 57 (1984) was used.

Female mice BALB/C weighing 18–20 g were purchased from Bomholdtgaard Breeding and Research Centre, DH-8680 Ry, Denmark. The animals were randomized in groups of five animals.

Mice were sensitized day 0 by epicutaneous application of 150 μl of absolute ethanol-aceton (3:1) solution containing 3% oxazolone (4-ethoxymethylene-2-phenyloxazol-5-one) on the shaved thorax and abdomen. Seven days after the sensitization (day 7) both ears of all mice were challenged on both sides by topical application of 20 μl of 1% oxazolone in peanut oil. Ear thickness was measured prior to 0 hrs and 24 hrs after challenge, using an Oditest spring caliper (Kröplin, Hessen, FRG). The test compounds were administered, suspended in aqueous methocel solution in a volume of 10 mg/kg, by gastric intubation once daily on days 0, 1, 2 and 3. The control animals received the same volume of aqueous methocel solution by gastric intubation.

The results are expressed in percent increase of the ear thickness of the animals treated with the test compounds as compared with the control animals treated with the vehicle.

TABLE 1

| Preliminary results from the oxazolone induced hypersensitivity test in mice: | | |
|---|---|---|
| Compound | Dose mg/kg p o | Increase of ear thickness, % 24 hrs |
| 1:1 | 4 × 10 | 75.7 |
| 1:2 | 4 × 10 | 79.6 |
| Roquinimex* | 4 × 10 | 47.3 |

*N-methyl-N-phenyl-1,2-dihydro-4-hydroxy-1-methyl-2-oxo-quinoline-3-carboxamide.

The following compounds were also tested in the oxazolone induced hypersensitivity test in mice as described above and produced an increase in ear thickness:

N-methyl-N-(4-methoxyphenyl)-1,2-dihydro-4-hydroxy-2-oxo-quinoline-3-carboxamide (1:2)

N-methyl-4-phenyl-1,2-dihydro-4-hydroxy-6-methoxy-2-oxo-quinoline-3-carboxamide (1:3)

N-methyl-N-(4-methoxyphenyl)-1,2-dihydro-4-hydroxy-6-methoxy-2-oxoquinoline-3-carboxamide (1:4)

N-methyl-N-(3-methoxyphenyl)-1,2-dihydro-4-hydroxy-7-methoxy-2-oxoquinoline-3-carboxamide (1:5).

N-methyl-N-phenyl-1,2-dihydro-4,6-dihydroxy-2-oxo-quinoline-3-carbox amide (2:2)

N-methyl-N-phenyl-1,2-dihydro-4,7-dihydroxy-2-oxo-quinoline-3-carbox amide (2:3)

N-methyl-N-(4-hydroxy-phenyl)-1,2-dihydro-4-hydroxy-2-oxo-quinoline-3-carboxamide (2:4)

N-methyl-N-(4-hydroxy-phenyl)-1,2-dihydro-4,6-dihydroxy-2-oxo-quino line-3-carboxamide (2:5)

We claim:

1. A novel compound having the formula

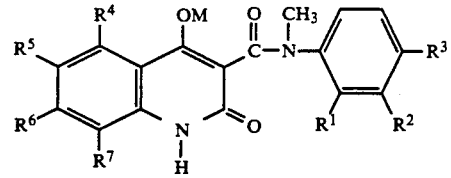

wherein $R^1$, $R^2$, $R^3$, $R^4$, $R^5$, $R^6$ and $R^7$ are selected from the group consisting of hydrogen, hydroxy and methoxy, wherein at most one of $R^1$, $R^2$ and $R^3$ and at most one of $R^4$, $R^5$, $R^6$ and $R^7$ are selected from the group consisting of hydroxy and methoxy; and M is selected from the group consisting of hydrogen and pharmaceutically acceptable inorganic or organic cations or tautomeric forms thereof.

2. A compound according to claim 1, wherein said compound is N-methyl-N-phenyl-1,2-dihydro-4-hydroxy-2-oxo-quinoline-3-carboxamide.

3. A compound according to claim 1, wherein said compound is N-methyl-N-(4-methoxyphenyl)-1,2-dihydro-4-hydroxy-2-oxo-quinoline-3-carboxamide.

4. A compound according to claim 1, wherein said compound is N-methyl-4-phenyl-1,2-dihydro-4-hydroxy-6-methoxy-2-oxo-quinoline-3-carboxamide.

5. A compound according to claim 1, wherein said compound is selected from the group consisting of N-methyl-N-(4-methoxyphenyl)-1,2-dihydro-4-hydroxy-6-methoxy-2-oxo-quinoline-3-carboxamide and N-methyl-N-(3-methoxyphenyl)-1,2-dihydro-4-hydroxy-7-methoxy-2-oxo-quinoline-3-carboxamide.

6. A compound according to claim 1, wherein said compound is N-methyl-N-(4-methoxyphenyl)-1,2-dihydro-4-hydroxy-2-oxo-quinoline-3-carboxamide.

7. A compound according to claim 1, wherein said compound is N-methyl-N-phenyl-1,2-dihydro-4,6-hydroxy-2-oxo-quinoline-3-carboxamide.

8. A compound according to claim 1 wherein said compound is selected from the group consisting of N-methyl-N-phenyl-1,2-dihydro-4,7-dihydroxy-2-oxo-quinoline-3-carboxamide and N-methyl-N-(4-hydroxyphenyl)-1,2-dihydro-4,6-hydroxy-2-oxo-quinoline-3-carboxamide.

* * * * *